(12) United States Patent
Keller

(10) Patent No.: US 8,256,646 B2
(45) Date of Patent: Sep. 4, 2012

(54) DEVICE AND METHOD FOR STORING, MIXING AND DISPENSING COMPONENTS

(75) Inventor: Wilhelm A. Keller, Merlischachen (CH)

(73) Assignee: Medmix Systems AG, Rotkreuz (CH)

( * ) Notice: Subject to any disclaimer, the term of this patent is extended or adjusted under 35 U.S.C. 154(b) by 369 days.

(21) Appl. No.: 12/310,158

(22) PCT Filed: Aug. 17, 2007

(86) PCT No.: PCT/CH2007/000406
§ 371 (c)(1),
(2), (4) Date: Feb. 13, 2009

(87) PCT Pub. No.: WO2008/022481
PCT Pub. Date: Feb. 28, 2008

(65) Prior Publication Data
US 2009/0314803 A1    Dec. 24, 2009

(30) Foreign Application Priority Data

Aug. 22, 2006 (CH) .................................. 1337/06

(51) Int. Cl.
*B67D 7/70* (2010.01)
(52) U.S. Cl. .................................... 222/136; 222/145.6
(58) Field of Classification Search .................. 222/136, 222/145.1, 145.5, 145.6, 129; 604/82–92; 206/219–222
See application file for complete search history.

(56) References Cited

U.S. PATENT DOCUMENTS

| 3,195,778 A | | 7/1965 | Coates | |
|---|---|---|---|---|
| 3,370,754 A | * | 2/1968 | Schumann et al. | 222/132 |
| 3,489,147 A | * | 1/1970 | Shaw | 604/88 |
| 4,055,177 A | * | 10/1977 | Cohen | 604/88 |
| 4,059,109 A | * | 11/1977 | Tischlinger | 604/88 |
| 4,171,698 A | * | 10/1979 | Genese | 604/88 |
| 4,254,768 A | * | 3/1981 | Ty | 604/518 |
| 4,464,174 A | * | 8/1984 | Ennis | 604/90 |
| 4,750,615 A | | 6/1988 | Kaufeler | |
| 4,808,006 A | | 2/1989 | Kaufeler | |
| 5,476,449 A | * | 12/1995 | Richmond | 604/87 |
| 5,549,380 A | | 8/1996 | Lidgren et al. | |
| 6,017,349 A | | 1/2000 | Heller et al. | |
| 6,149,628 A | * | 11/2000 | Szapiro et al. | 604/191 |
| 7,216,761 B2 | | 5/2007 | De Vries | |
| 7,879,002 B2 | * | 2/2011 | Jessop | 604/91 |

(Continued)

FOREIGN PATENT DOCUMENTS

CA    541 481    9/1973

(Continued)

*Primary Examiner* — Lien Ngo
(74) *Attorney, Agent, or Firm* — Foley & Lardner LLP

(57) ABSTRACT

A device for storing, mixing, and dispensing components that has at least one container and a transferor configured to transfer a first, liquid component into a second, powdery component, a dispensing piston configured to dispense mixed materials, a valve assembly arranged between the first, liquid component and the second, powdery component, and a closure element. The first, liquid component and the second, powdery component are located in the at least one container, and the transfer device arranged between the first, liquid component and the second, powdery component is designed as a sealing passage piston. Such a multicomponent syringe has a significantly reduced volume as compared to the multicomponent syringes of the prior art but nevertheless offers a simple and safe handling besides the required safety with regard to separate storage and hygiene.

11 Claims, 3 Drawing Sheets

U.S. PATENT DOCUMENTS

| | | | |
|---|---|---|---|
| 7,951,108 B2 * | 5/2011 | Harper et al. .................. | 604/82 |
| 2007/0211563 A1 | 9/2007 | De Vries | |

FOREIGN PATENT DOCUMENTS

| DE | 85 13 346 | 6/1985 |
|---|---|---|
| DE | 44 09 610 | 9/1995 |
| DE | 101 51 104 | 4/2003 |
| EP | 0 225 294 | 6/1987 |
| EP | 0 674 888 | 10/1995 |
| EP | 0 882 436 | 12/1998 |
| EP | 1 005 900 | 6/2000 |
| WO | WO-97/18031 | 5/1997 |
| WO | WO-2005/053581 | 6/2005 |

* cited by examiner

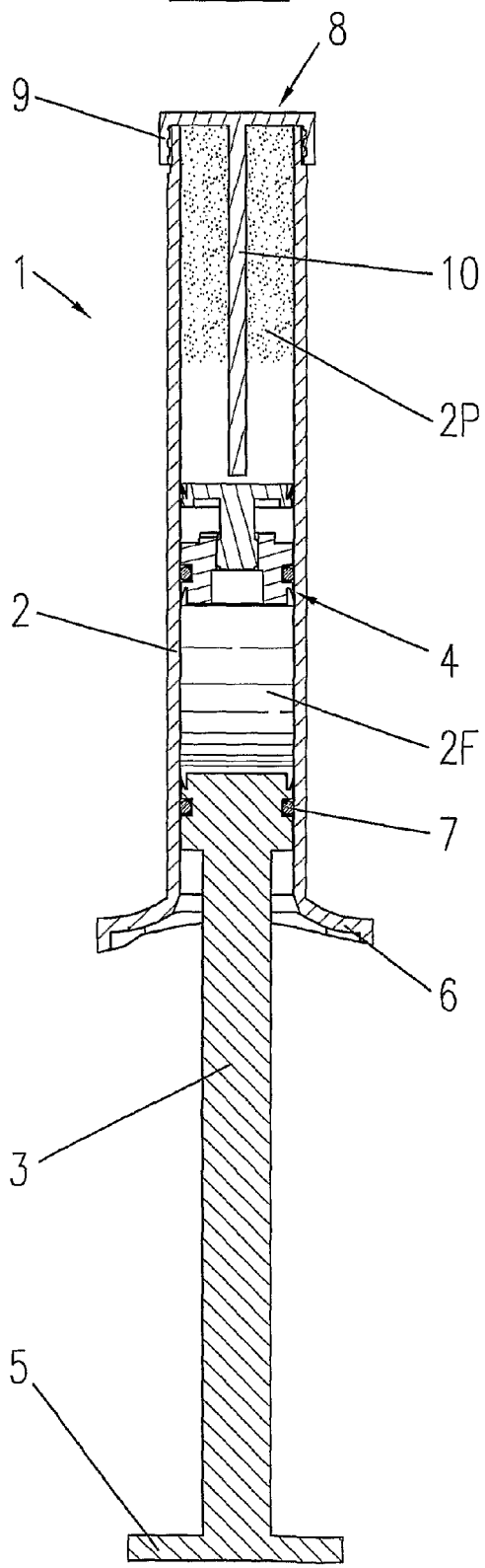
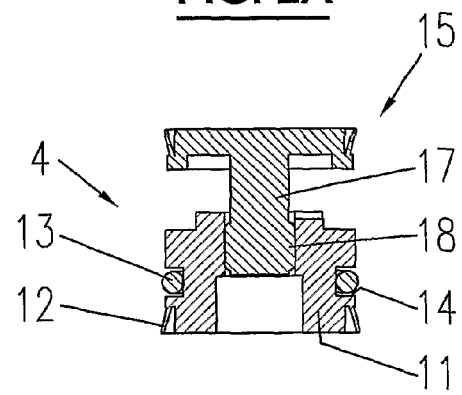
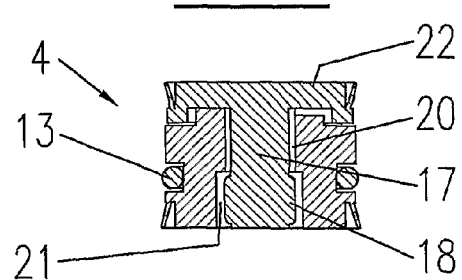
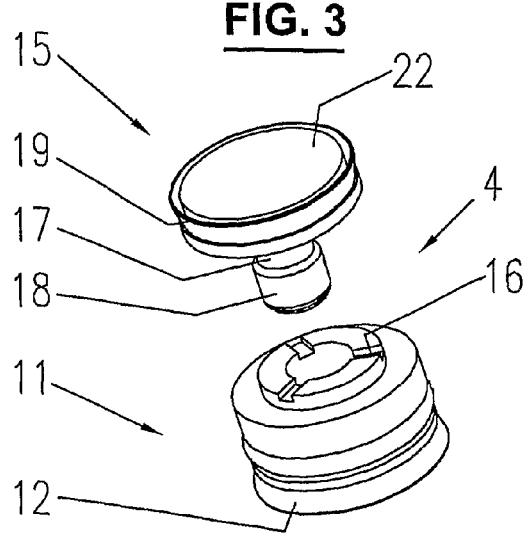

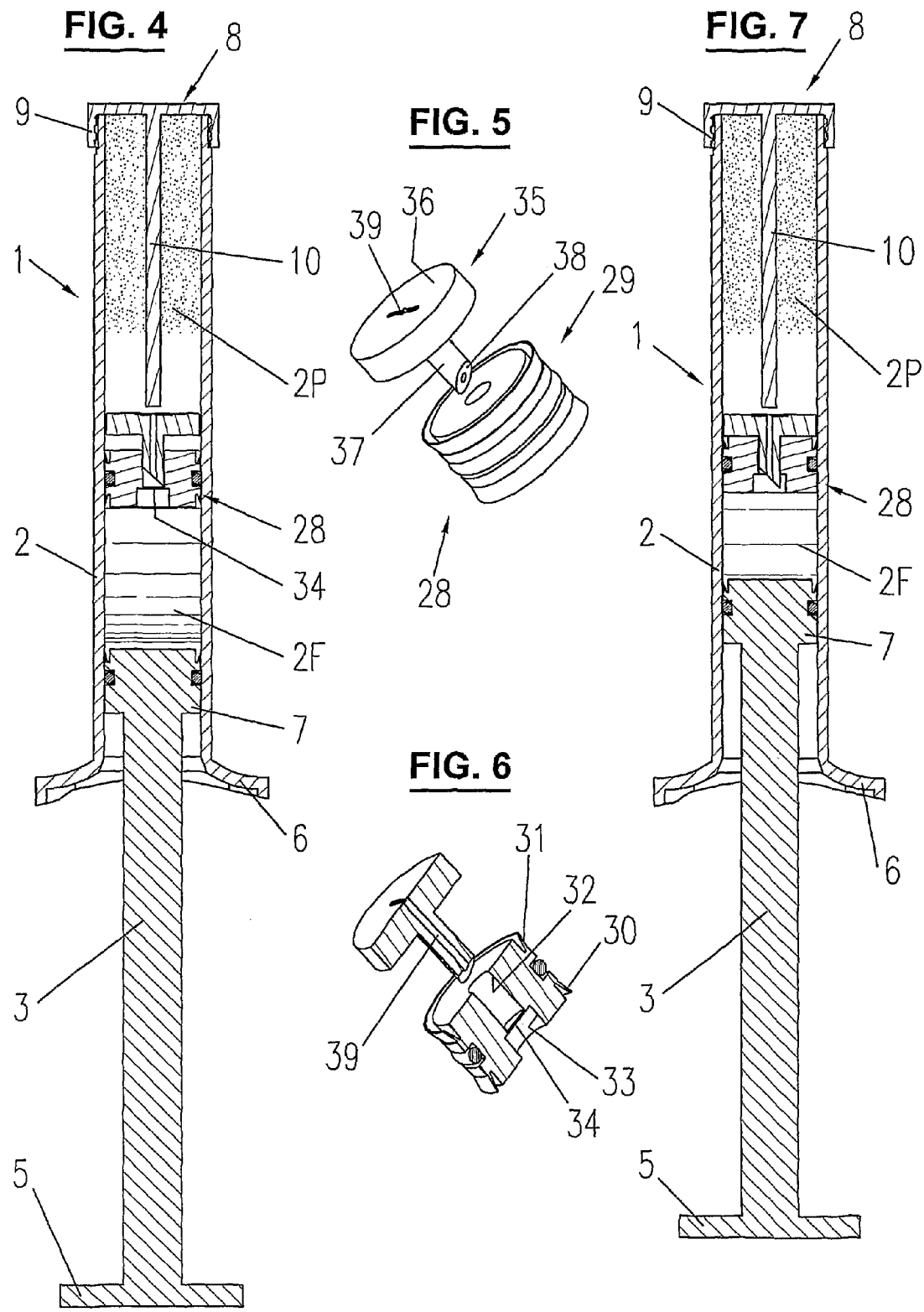

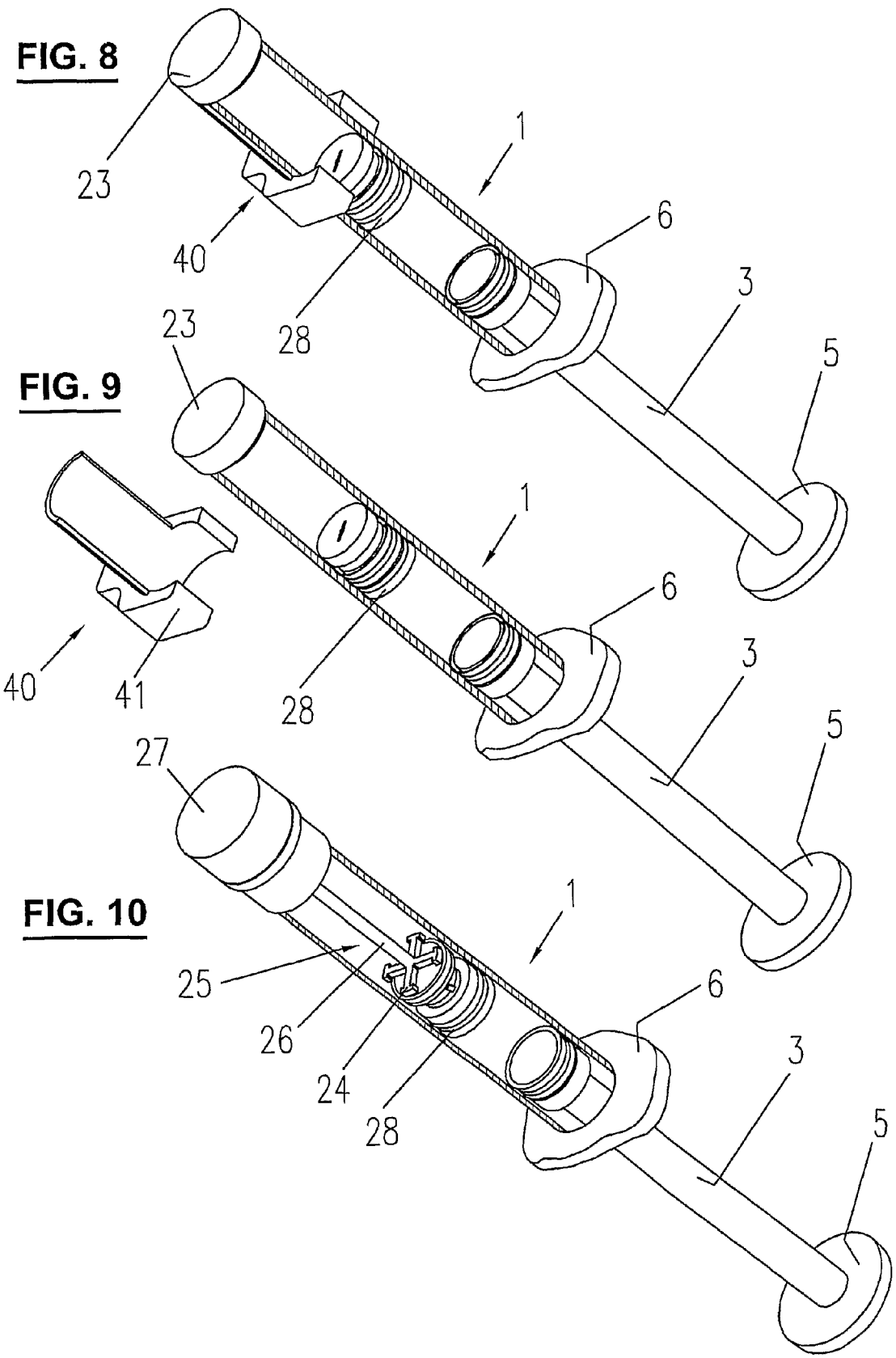

DEVICE AND METHOD FOR STORING, MIXING AND DISPENSING COMPONENTS

This application is the National Phase of PCT/CH2007/000406, filed Aug. 17, 2007, which claims priority to Switzerland Application No. 01337/06, filed Aug. 22, 2006. The contents of the foregoing applications are incorporated by reference in their entirety.

The present invention relates to a device and method for storing, mixing, and dispensing components, comprising at least one container and means for the transfer of a first, liquid component into a second component.

A device of this kind is known from WO2005/018830 to the applicant of the present invention. The first component is generally a liquid, and the second component may be a powdery, porous, or granular bone replacement material, bone cement, or lyophilisate, or a similar material for use in medicine, dentistry, or industry. In this device of the prior art, the individual components are contained in respective adjacent containers, a valve assembly being provided between these two containers for selectively connecting the containers to one another or to the outlet.

In a variant, the container for the second component comprises a mixing arrangement that is separated from the dispensing means and includes a mixing rod that is movable back and forth and provided with a mixing member.

While this known device is suitable for different volumes, it has been found to be advantageous for smaller volumes to provide a smaller and simpler device while the two components should be brought together and mixed under hygienic conditions without being transferred between containers in the open or removed from a sterile packaging.

U.S. Pat. No. 3,195,778 A discloses a storage and mixing cartridge comprising a partition separating two compartments, the said partition having a sealing edge in contact with the inner wall and a passage therethrough. In the passage there is a dasher with a handle at one end and a prong at the other end for cutting through the partition when retiring the dasher.

CH 541 481 A discloses a dispenser for fluids with two compartments and two concentric arranged pistons for transferring one component into the other. The mixing is effectuated by the back-and-forth movement of the pistons after which the pistons are locked together for the dispensing of the mixture.

DE 85 13 346 U1 discloses a dispensing cartridge with two aligned compartments and a separating ring with inner cover between. In the cover a mixing tube is inserted which movement causes the cover to be lift off from the ring so that one component can flow into the other for being mixed. After the mixing process a piston presses the mixture through the tube to the dispensing outlet.

EP 0 225 294 A2 discloses a dispensing device with two compartments and a membrane for separating the substances and a means for perforating the membrane. The means for perforating the membrane is a handle with a solid disk having points, serving also as mixing device.

On this background, it is an object of the present invention to provide for a device for storing, mixing, and dispensing components that fulfills the same requirements regarding storage and mixture of components as well as the known hygienic requirements of the prior art and that allows an easy dispensing of the two components with a reduced total volume.

The invention will be explained in more detail hereinafter with reference to drawings of exemplary embodiments.

FIG. 1 shows a first exemplary embodiment of the device according to the invention in a longitudinal section, FIG. 2A shows the passage piston of FIG. 1 in a first position, FIG. 2B shows the passage piston of FIG. 1 in a second position, FIG. 3 shows the passage piston of FIGS. 2A and 2B in a perspective view, FIG. 4 shows a second exemplary embodiment in analogy to FIG. 1 in a first position, FIG. 5 shows a second exemplary embodiment of the passage piston, FIG. 6 shows the passage piston in a sectional view, FIG. 7 shows the second exemplary embodiment of FIG. 5 in a second position, FIGS. 8 and 9 show an embodiment variant having stop means, and FIG. 10 shows an embodiment variant having a stirring arrangement.

The longitudinal section of FIG. 1 shows as a first exemplary embodiment a device 1 according to the invention that may be a syringe or cartridge, or a double syringe or cartridge, having a container 2 in which a dispensing piston 3 and a passage piston 4 are arranged one after the other. Dispensing piston 3 has a pressure rest 5 and container 2 has a retaining flange 6 on its inlet side in order to facilitate pushing in the dispensing piston. On its outlet side, dispensing piston 3 is provided with a seal accommodated in a groove, e.g. an O-ring 7.

Passage piston 4 divides storage container 2 into two chambers, i.e. chamber 2F containing liquid F, located between the passage piston and the dispensing piston, and chamber 2P for the second, powdery component P, located between the passage piston and the outlet. Outlet 8 is sealed by a screw closure 9, the closure alternatively being a snap closure or the like.

FIGS. 2A, 2B, and 3 show passage piston 4 in more detail. It is composed of a piston housing 11 and of a piston plunger 15, the piston housing having a sealing lip 12 on its inlet side and a following O-ring 13 seated in a groove 14 in the piston housing. The front face on its outlet side is provided with channels 16, in the present case three channels.

Piston plunger 15 is approximately mushroom-shaped in cross-section and has a pressure plate 22 with a sealing lip 19 that connects to a cylindrical portion 17 whose end is provided with a sealing cylinder 18 having an enlarged diameter. Cylindrical portion 17 with sealing cylinder 18 is located in a cylindrical bore 20 in the piston housing, bore 20 being followed on the inlet side by an enlarged bore 21.

In order to keep the passage piston or its pressure plate 22, respectively, from receding, it is supported according to FIG. 1 by a supporting post 10.

In order to transfer the liquid from liquid chamber 2F to powder chamber 2P, dispensing piston 3 is pushed toward the outlet, whereby a force is applied to piston housing 11 of passage piston 4 via the liquid. Since piston plunger 15 is supported on the outlet side, piston housing 11 is displaced on the cylindrical portion of piston plunger 15. As follows from a comparison of FIGS. 2B and 2A, a passage is thus formed and the liquid passes between sealing cylinder 18 and cylindrical portion 17 of the piston plunger and bore 20 and reaches channels 16.

Channels 16 direct the liquid outwards, from where it is subsequently transferred to powder chamber 2P between sealing lip 19 on pressure plate 22 and the container wall, the design of sealing lip 19 preventing a backflow of the liquid.

For dispensing, closure 9 with the supporting post is removed and the dispensing piston is further displaced toward the outlet.

If the resulting mixture has to be stirred, an embodiment having a stirring unit 25 is available which is shown in FIG. 10. According to this Figure, stirring unit 25 comprises a stirring paddle 24 whose rod 26 passes through closure 9 and is fastened to a turning knob 27. At the same time, the shaft here also serves as the supporting post for holding back the piston plunger. Turning knob 27 is connected to the closure by a predetermined breaking point or a snap connection. For mixing and stirring, turning knob 27 of the stirring unit is detached from the closing cap, and mixing is then achieved by a rotary and longitudinal movement of the stirring paddle.

After the mixing operation, the stirring unit including the turning knob and the closure are removed from the container and the mixed liquid is dispensed through the action of the dispensing piston that pushes the passage piston and thus the mixture toward the outlet.

Optionally and according to the intended purpose, a number of different application instruments may be connected to the container outlet.

In FIGS. 4 to 7, a second exemplary embodiment is depicted where instead of a passage piston having a piston plunger with a sealing cylinder, a passage piston having a membrane and a piston plunger with a spike is arranged between the liquid and the powder chamber, the membrane being pierced upon actuation of the dispensing piston.

Syringe 1 with container 2 and chambers 2F and 2P are the same as in the first exemplary embodiment, and so is dispensing piston 3.

Passage piston 28 has a piston housing 29 that may be similar to piston housing 11 or in contrast thereto may have respective sealing lips 30 and 31 at both ends, but no channels. The two bores 32 and 33 are similar to those of the first exemplary embodiment. At the transition from the narrower to the larger bore, a membrane 34 is provided.

Piston plunger 35 comprises a pressure plate 36 that connects to a spike 37 having a slanted cutting edge 38 on its front side and a through-going bore 39. The pressure plate may also have a sealing lip.

The comparison of FIGS. 4 and 7 shows that when the dispensing piston is pushed in, the piston housing is moved toward the outlet and the supported piston plunger, i.e. its cutting edge will pierce the membrane, thereby allowing the liquid to reach powder chamber 2P.

In FIGS. 8 and 9, an embodiment variant having an externally acting stop is shown. This stop member 40 is used when closure 23 cannot be provided with a supporting post e.g. for lack of space. Stop member 40 has clamping jaws 41 that deform the container and thus prevent a displacement of the pressure plate of the transfer piston.

Based on the above examples, still other variants of a passage piston are conceivable, e.g. with a unidirectional opening device of the valve type or with a piston plunger having a plurality of passages instead of one central passage.

The invention claimed is:

1. A device for storing, mixing, and dispensing components, comprising;
    at least one container;
    a dispensing piston configured to transfer a first, liquid component into a second component to form mixed materials;
    a closure element; and
    a transfer device arranged between the first, liquid component and the second component, wherein the transfer device comprises a passage piston that is actuatable from a sealing position to an open position, the passage piston comprising a piston housing and a piston plunger;
    wherein the first, liquid component and the second component are located in the at least one container,
    wherein the piston housing is internally provided with a longitudinal bore having a first diameter and a second diameter,
    wherein the first diameter on an inlet side is greater than the second diameter, and
    wherein the piston plunger has a cylindrical portion with a following sealing cylinder such that when the piston plunger is pushed in, the following sealing cylinder enters into the first diameter of the longitudinal bore, thereby allowing the liquid to flow through.

2. The device according to claim 1, wherein the piston housing further comprises at least one external sealing lip.

3. A device according to claim 1, wherein the piston plunger further comprises a pressure plate with an external seal.

4. The device according to claim 1, wherein the dispensing piston further comprises a sealing element on an outlet end of the dispensing piston and a pressure rest on another end of the dispending piston.

5. The device according to claim 1, further comprising a stirring unit, wherein the stirring unit comprises a stirring paddle whose rod passes through the closure element and is fastened to a detachable turning knob.

6. A method of operating a device for storing, mixing, and dispensing components with a dispensing piston, a passage piston including a piston housing and a piston plunger, wherein the piston housing is internally provided with a longitudinal bore having a first diameter and a second diameter, the first diameter on an inlet side being greater than the second diameter, and wherein the piston plunger has a cylindrical portion with a following sealing cylinder, the method comprising:
    pushing the dispensing piston toward an outlet;
    displacing the piston housing toward the outlet;
    entering the following sealing cylinder into the first diameter of the longitudinal bore;
    passing liquid between the sealing cylinder and a wall of the narrow bore; and
    reaching a powder container via a pressure plate of the piston plunger.

7. The method of operating the device according to claim 6, further comprising:
    detaching a stirring unit from the a closure; and
    actuating the stirring unit by turning and pulling, whereupon the stirring unit and the closure are removed and the dispensing piston is actuated to dispense the mixture.

8. The method of operating the device according to claim 6, further comprising:
    pushing the dispensing piston toward the outlet, whereby the piston housing is displaced toward the outlet and a membrane is pierced and wherein the liquid reaches a powder chamber through a hollow spike.

9. The device according to claim 1, wherein on an outlet side, the movement of the piston plunger is limited by a supporting element.

10. The device according to claim 9, wherein the supporting element comprises a supporting post that is fastened to the closure element of the at least one container or of a stirring rod.

11. The device according to claim 9, wherein the supporting element comprises a stop member that is configured to be clamped onto the at least one container.

* * * * *